United States Patent [19]

Buon et al.

[11] Patent Number: 4,494,548

[45] Date of Patent: Jan. 22, 1985

[54] ULTRASONIC SECTOR SCANNER

[75] Inventors: Georges Buon, Flushing; Howard Fidel, Hartsdale, both of N.Y.

[73] Assignee: Biosound, Inc., Indianapolis, Ind.

[21] Appl. No.: 370,014

[22] Filed: Apr. 20, 1982

[51] Int. Cl.[3] .................................... A61B 10/00

[52] U.S. Cl. .................................... 128/660; 128/661; 73/620

[58] Field of Search .................................... 128/660–663; 73/620, 629, 639

[56] References Cited

U.S. PATENT DOCUMENTS

| | | | |
|---|---|---|---|
| 3,741,004 | 6/1973 | Posakory | 73/620 |
| 3,955,561 | 5/1976 | Eggleton | 128/660 |
| 4,034,744 | 7/1977 | Goldberg | 128/660 |
| 4,120,291 | 10/1978 | Paton et al. | 73/620 |
| 4,151,834 | 5/1979 | Sato et al. | 73/619 X |
| 4,215,585 | 8/1980 | Kunii et al. | 128/660 X |
| 4,275,597 | 6/1981 | Quedens et al. | 128/660 X |
| 4,374,525 | 2/1983 | Baba | 128/660 |
| 4,399,822 | 8/1983 | Theumer | 128/660 |

*Primary Examiner*—Kyle L. Howell
*Assistant Examiner*—Francis J. Jaworski
*Attorney, Agent, or Firm*—Woodard, Weikart, Emhardt & Naughton

[57] ABSTRACT

An ultrasonic sector scanner uses a transducer mounted within an ultrasonic transmitting medium with a rotating cam surface bearing against the transducer for inducing a rocking motion of the transducer between a pair of predetermined limit positions. The cam surface if rotatably driven by a Cardan joint mounted on a motor output shaft to produce an angular velocity of the transducer wherein the relationship between the angle of the transducer and the input shaft to the Cardan joint is a linear function. The position of the transducer is monitored by a code wheel connected to the motor drive to allow either a constant motor rotation or a selective angular positioning of the transducer.

6 Claims, 2 Drawing Figures

ULTRASONIC SECTOR SCANNER

BACKGROUND OF THE INVENTION

1. Field of the Invention

The present invention relates to ultrasonic diagnostic apparatus. More specifically, the present invention is directed to a diagnostic probe having an ultrasonic sector scanner.

2. Description of the Prior Art

Ultrasonic analysis is a commonly used technique for producing a tomogram for viewing internal anatomy. This technique has particular utility in so-called real time imaging whereby the images are produced sequentially at a rate sufficiently high to enable dynamic visualiztion of the motion of internal organs. The irradiation of the human tissue by the ultrasonic wave produces output signals from the scanning device by differing attenuation of the reflected ultrasonic wave between differences in structure of the internal organs. Thus, the tomogram is obtained by utilizing the echo of the ultrasonic wave. In utilizing such an ultrasonic diagnostic apparatus, the proximity method uses a technique wherein an ultrasonic probe is placed in contact with the surface of the body under examination while isolating the scanning transducer from the point of contact. Such a technique enables the ultrasonic beam to be scanned through the space between two adjacent ribs or any other area which would allow transmission of the ultrasonic beam. In producing such a diagnostic device, the apparatus must be capable of being handheld in operation particularly where the proximity method is used in the real time cardiac imaging. In order to achieve the direct contact between the probe and the human anatomy, the ultrasonic probe is immersed in a medium capable of transmitting the ultrasonic beam and allowing a scanning motion of the transducer while the surface of the probe which seals the transmitting medium within the probe must also be transparent to the ultrasonic beam and match the acoustic properties of human tissue.

DESCRIPTION OF THE INVENTION

An object of the present inventon is to provide an improved diagnostic probe having a linear angular motion of a transducer for sector scan operation.

In accomplishing this and other objects, there has been provided, in accordance with the present invention an ultrasonic probe having an ultrasonic transducer mounted for rotation about an axis perpendicular to the ultrasonic transducer. A cam surface is arranged to contact the ultrasonic transducer while the cam surface is driven by a Cardan joint about an axis perpendicular to the axis of rotation of the ultrasonic transducer to induce an oscillation of the transducer about its axis of rotation wherein the relationship between the angle of the transducer and the input shaft to the Cardan joint is a linear function. A code wheel is attached to a motor drive for the cam to provide a measure of the position of the transducer. The transducer is electrically connected to associated equipment for energizing and monitoring of reflected energy.

DESCRIPTION OF THE DRAWINGS

A better understanding of the present invention may be had when the following detailed description is read in connection with the accompanying drawings, in which.

DESCRIPTION OF THE PREFERRED EMBODIMENT

Figure 1:
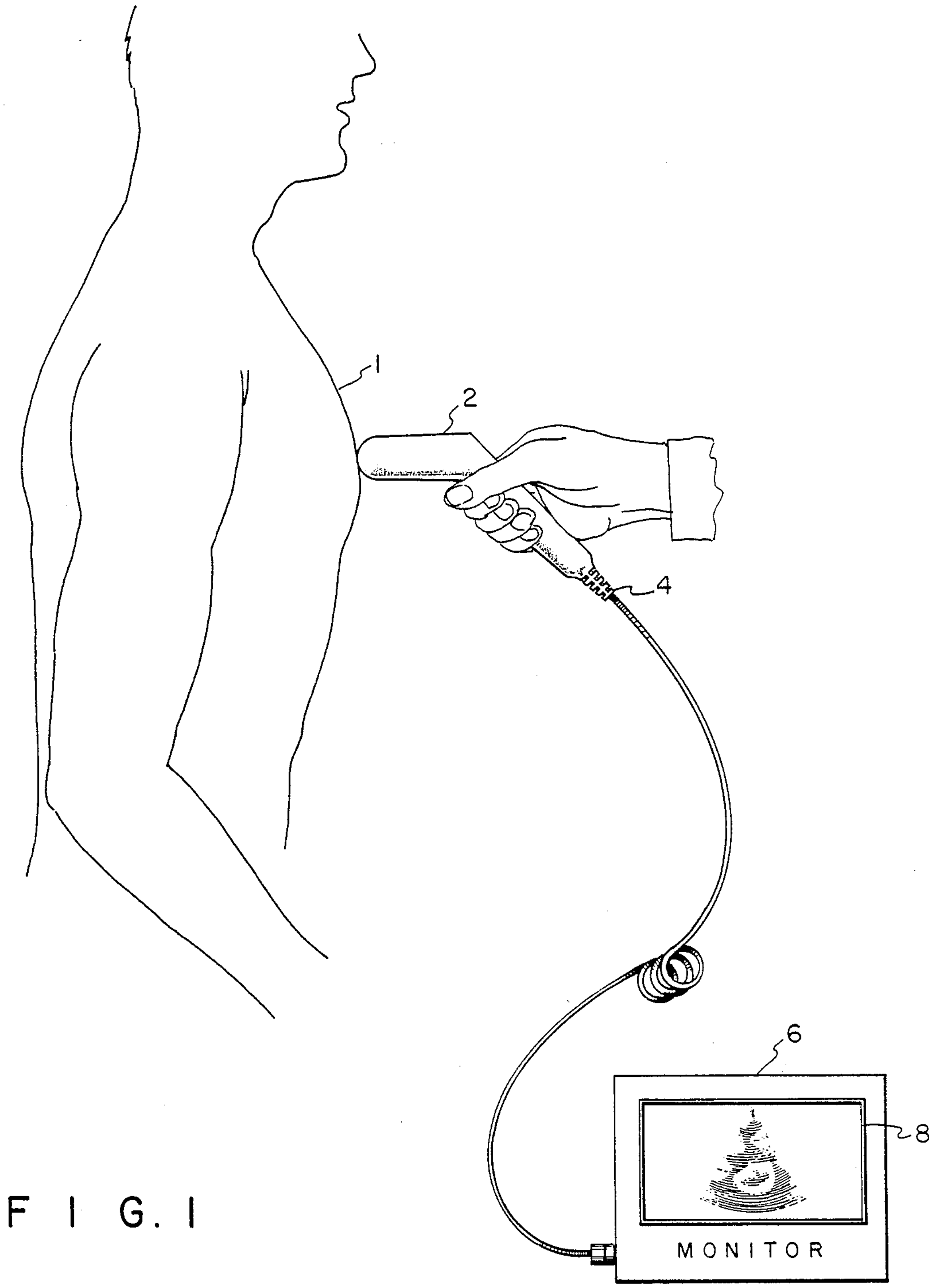
FIG. 1 is a pictorial illustration showing the ultrasonic scanner of the present invention in use and, FIG. 2 is a cross sectional illustration of the ultrasonic scanner shown in FIG. 1 and embodying an example of the present invention.

Referring to FIG. 1 is more detail, there is shown a subject 1 to which an ultrasonic analysis is to be applied. In the illustration, the subject 1 is a portion of human anatomy, e.g., the portion of the chest adjacent to the heart whereby a real time cardiac imaging may be obtained. The front surface of an ultrasonic probe 2 is placed in contact with the skin of the subject 1. The ultrasonic probe 2 is a handheld device which is connected by a cable 4 to associated equipment 6 which may include a CRT monitor screen 8 providing a visual representation of the tomogram produced by the ultrasonic analysis.

Figure 2:
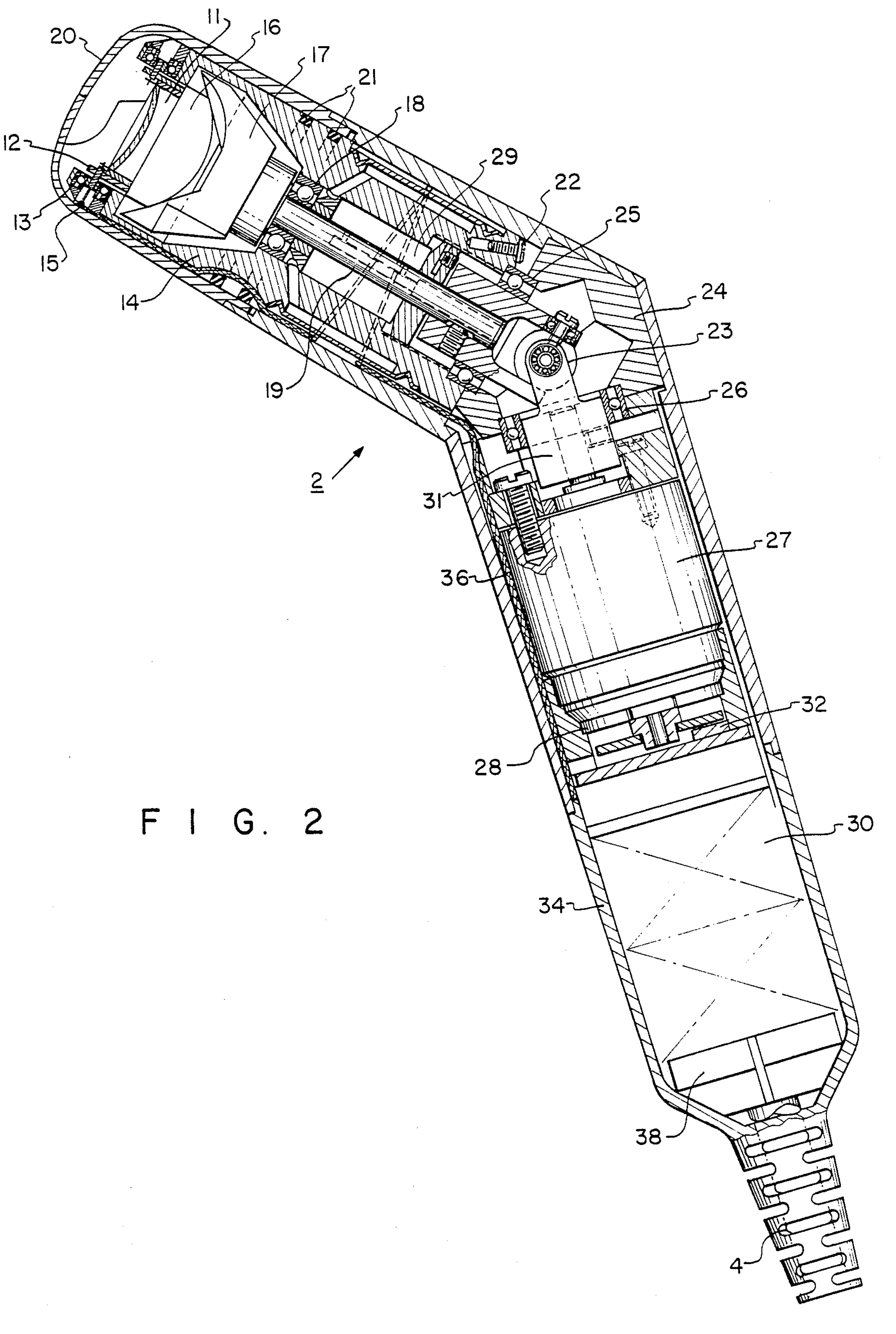

In FIG. 2, there is shown a cross sectional illustration of the ultrasonic probe shown in FIG. 1 and embodying an example of the present invention. The probe 2 includes an ultrasonic transducer 11 of the piezoelectric type, e.g., a 3.0 MHz, 13 mm diameter, 7 CM focus, one-quarter wave matched transducer, mounted in a yoke 12. The yoke 12 has an axis of rotation or oscillation defined by an extension of the yoke 12 supported by a ball bearing 13 mounted within a support extension 14. Electrical connections are made to the transducer 11 by copper springs 15. The copper springs 15 may be of beryllium copper wire having a 0.005 inch diameter wire wound with a 0.025 inch diameter winding and a 0.160 inch length. Attached to the back of the transducer yoke 12 is a cam follower 16 which may be made of any suitable material, e.g., nylon. The cam follower 16 is arranged to ride on a cam 17 mounted on one end of a shaft 19 for coaxial rotation therewith. The axis of rotation of the shaft 19 and the cam 17 is arranged to be perpendicular to the axis of oscillation of the yoke 12. The front face 20 of the probe 2 is a hybrid acoustic window and cover wherein the area of the face 20 which is to be in contact with the skin of the patient is made of a sonically transparent material such as a so-called urethane U-17-1 made by ATS Labs of South Norwalk, Conn. The remainder of the face 20 is a cover made of an acoustic absorber material such as PRC 1538 manufactured by Product Research and Chemicals, Inc. of Glouster City, N.J. The space between the transducer 11 and the inside surface of the face 20, i.e., the front half of the probe 2, is filled with a fluid having an acoustic impedance and acoustic velocity matching those of human tissue, i.e., $1.63\times10^5$ Rayl and $1.54\times10^3$ m/sec. This fill fluid must also be capable of lubricating the mechanism which it contacts, i.e., the bearings 13 and 18, the cam 13, etc. and chemical compatible with the materials within the probe to which it is exposed as well as being electrically insulating. An example of such a fluid is composed of 71% propylene glycol and 29% Poly G-200. This fluid may be admitted within the probe 2 by fill plug 22. A pair of O-rings 21 are arranged to seal the internal support body 14 to the inside surface of the probe 2. In order to complete the fluid isolation of the front half of the probe, a ferro-fluid seal 29 such as that manufactured by Ferrofluidics, Nashua, N.H. is arranged to surround the shaft 19 behind the bearing 18.

The end of the shaft 19 opposite to the end connected to the cam 17 is coaxially connected to one side of a Cardan joint 23 which is retained in a 45° block 24 by bearings 25 and 26. The other side of the Cardan joint 23 is connected to one end of a drive shaft 31 of a motor 27 for coaxial rotation therewith. The other end of the motor shaft 31 extending outwardly from the other end of the motor 27 is connected to a tachometer disc 28. The position of the tachometer disc 28 is read by a conventional sensing device 32 to provide an output signal indicative of the rotational position of the motor shaft. An electronic circuit housing 30 is located adjacent to the motor 27 and disc 28 in a handle portion 34 of the scanner 2 to provide the electronic circuitry for energizing the transducer 11, decoding the signals received by transducer 11, operating the motor 27, decoding the signals from the sensing device 32, etc., such circuits being well-known in the art. Accordingly, a further discussion of those circuits, which do not form a portion of the invention disclosed herein, is believed to be unnecessary for a complete understanding of the present invention. The circuits in the circuit housing 30 are connected to the springs 15 by an internal electrical cable 36 and to an electrical connector 38 to provide an electrical connection to the probe cable 4.

In operation, the probe 2 uses the piezoelectric transducer 11 in a yoke 12 which is oscillated by the cam 17 to produce a sector scan of the acoustic signal. The displacement angle of the transducer 11 can be varied from approximately 15° to 45° by changing the characterized surface of the cam 17, i.e., the cam angle. The shaft 19 that turns the cam 17 has its angular velocity modulated by the Cardan joint 23. This is effective to linearize the angular velocity of the transducer 11 over its effective range of oscillation, i.e., the relationship between the angle of the transducer 11 and the input shaft 31 to the Cardan joint is a linear function. Thus a derivation of the cam motion produced by the motion of the Cardan joint produces a relationship wherein cam motion equals $\alpha \text{ Sin } [\tan^{-1} [(1/\sqrt{2}) \tan \beta(t)]]$ where $\alpha$ is the transducer angle and $\beta$ is the driving shaft angle. Substitution of cams for the cam 17 can produce a sector scan up to 90° while the scan is linear, i.e., the relationship between the angle of the transducer 11 and the input shaft 31 is a linear function, over substantially the entire sector scan, e.g., 80° of linear scan for a 90° sector scan. The incremenal encoder 32 provides a signal representative of the transducer position so that the transducer 11 can be operated in a servo-locked mode. The encoder disc 28 preferably has three tracks, i.e., a sine track, a cosine track and a reference track. This allows a determination of the absolute position of the transducer 11 to be determined whereby the motor 27 can be either operated at a constant velocity or positioned at a desired fixed angular location.

Accordingly, it may be seen that there has been provided, in accordance with the present invention, an improved diagnostic probe having an ultrasonic sector scanner exhibiting a linear angular motion.

The embodiments of the invention in which an exclusive property or privilege is claimed are defined as follows:

1. A diagnostic probe comprising:

a transducer means for supplying and receiving a diagnostic energy beam, scanning means for producing a sector scan of said transducer means, said scanning means including a cam means and an input shaft rotatable about a first fixed axis, and cam follower means in contact with said cam means and said transducer means for translating rotation of said cam means into oscillation of said transducer means about a second fixed axis, drive means for said scanning means including a motor means and Cardon joint, and a driveshaft means connecting said motor means to said Cardon joint, said scanning means input shaft being connected to said Cardon joint and serving as the output shaft therefrom, said driveshaft means and said input shaft being at a fixed predetermined angle at said joint, said scanning means cam and cam follower means being adapted to compensate for variations in rotational angular velocity of said scanning means input shaft due to the said predetermined Cardon joint angle whereby a linear relationship is maintained during transducer scanning between the change in transducer means scan angle as defined by the angle formed between the scan axis during scan motion and the scan axis at a fixed reference orientation, and the change in angle of rotation of said driveshaft means relative to a fixed reference rotational position, whereby linear sector scanning is enacted, and housing means for providing an enclosure for said transducer means, said scanning means and said drive means while allowing entry and exit of said energy beam and a connection of said diagnostic probe to associated equipment.

2. A diagnostic probe as set forth in claim 1 wherein said transducer means includes an ultrasonic transducer whereby said energy beam is an ultrasonic beam.

3. A diagnostic probe as set forth in claim 1 wherein said scanning means includes a yoke means for mounting said transducer means, said cam follower means in contact with said cam means and said yoke means for translating a rotation of said cam means into an oscillation of said transducer means about said second fixed axis.

4. A diagnostic probe as set forth in claim 3 wherein said first and second axis are mutually orthogonal.

5. A diagnostic probe as set forth in claim 4 wherein said drive means includes means for energizing said transducer means to produce said energy beam and means for analyzing said energy beam receiving by said transducer means.

6. A diagnostic probe as set forth in claim 1 wherein said drive means including rotational position detector means for producing a signal representative of an angular position of said transducer means.

* * * * *